(12) United States Patent
Racz et al.

(10) Patent No.: US 8,034,047 B2
(45) Date of Patent: Oct. 11, 2011

(54) CATHETER CONNECTION HUB

(75) Inventors: N. Sandor Racz, Coppell, TX (US); Gary Bullard, Saratoga Springs, NY (US)

(73) Assignee: Custom Medical Applications, Inc., Johnstown, NY (US)

( * ) Notice: Subject to any disclaimer, the term of this patent is extended or adjusted under 35 U.S.C. 154(b) by 485 days.

(21) Appl. No.: 12/154,323

(22) Filed: May 21, 2008

(65) Prior Publication Data
US 2009/0292273 A1    Nov. 26, 2009

(51) Int. Cl.
*A61M 25/00* (2006.01)
(52) U.S. Cl. ......... 604/535; 604/247; 604/533; 604/534
(58) Field of Classification Search .................. 604/175, 604/534, 171, 533, 256, 163, 161, 535–284
See application file for complete search history.

(56) References Cited

U.S. PATENT DOCUMENTS

| | | |
|---|---|---|
| 3,920,215 A | 11/1975 | Knauf |
| 4,327,723 A | 5/1982 | Frankhouser |
| 4,378,013 A | 3/1983 | LeFevre |
| 4,613,329 A | 9/1986 | Bodicky |
| 4,834,719 A | 5/1989 | Arenas |
| 4,895,570 A | 1/1990 | Larkin |
| 4,929,236 A | 5/1990 | Sampson |
| 5,127,626 A | 7/1992 | Hilal et al. |
| 5,279,597 A | 1/1994 | Dassa et al. |
| 5,505,714 A | 4/1996 | Dassa et al. |
| 5,507,733 A | 4/1996 | Larkin et al. |
| D408,530 S | 4/1999 | Eliasen et al. |
| 5,968,011 A | 10/1999 | Larsen et al. |
| 5,993,437 A | 11/1999 | Roaz |
| 6,086,575 A | 7/2000 | Mejslov |
| 6,099,519 A * | 8/2000 | Olsen et al. ............... 604/534 |
| D433,503 S | 11/2000 | Powers et al. |
| 6,190,372 B1 | 2/2001 | Racz |
| 6,254,589 B1 | 7/2001 | Roaz |
| 6,332,874 B1 | 12/2001 | Eliasen et al. |
| 6,572,586 B1 | 6/2003 | Wojcik |
| 6,749,589 B1 | 6/2004 | Douglas et al. |

* cited by examiner

*Primary Examiner* — Theodore Stigell
*Assistant Examiner* — Brandy C Scott
(74) *Attorney, Agent, or Firm* — TraskBritt, P.C.

(57) ABSTRACT

Fluid communication to an end of a catheter is afforded through a connection hub selectively attachable thereto. The connection hub includes a catheter-receiving element and a fluid-coupling element that are relatively rotatable coaxially between one of two states by way of a determinant assembly feature. The first state is an unlocked state and the second state is a locked state. The unlocked state is for determinately receiving a catheter and the locked state is for determinately securing the catheter. A method of making a connection hub is also provided.

21 Claims, 8 Drawing Sheets

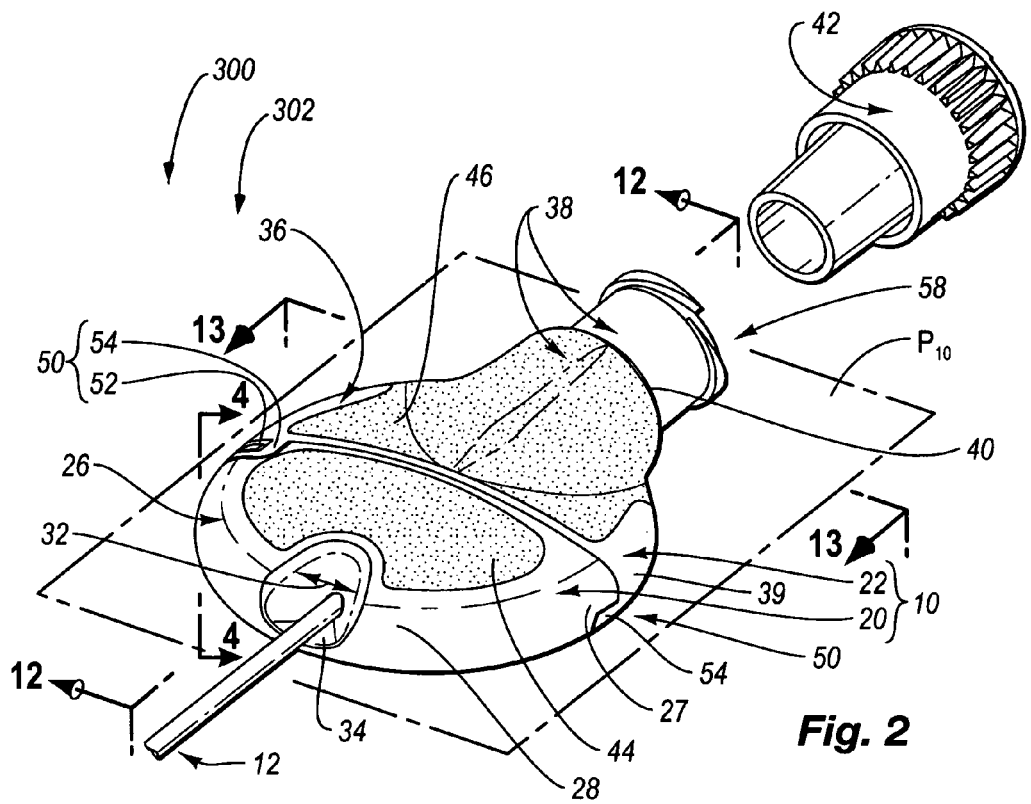
*Fig. 2*
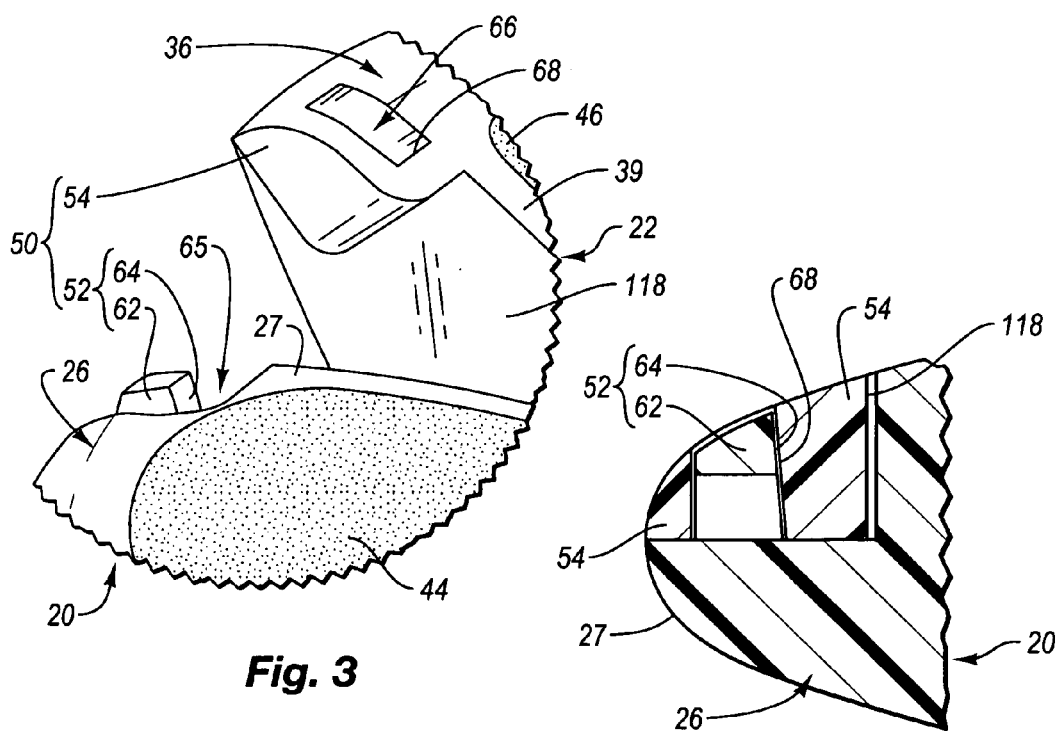
*Fig. 3*
*Fig. 4*

CATHETER CONNECTION HUB

FIELD OF THE INVENTION

This invention relates generally to medical devices, and, more particularly, to structures in connection hubs for determinant assembly with medical catheters. Generally, various embodiments of the invention relate to connection hubs attachable to a free end of a catheter to enable selective fluid communication with the interior of that catheter. More particularly, the invention relates to such connection hubs that include determinant assembly features as are attachable in the field at the time of use through manual manipulation by medical personnel.

BACKGROUND

Conventional catheter connection hubs, comprising a catheter receiving part and a fluid coupling part cooperatively engage to one another, allow a free end of a catheter to be inserted into the catheter receiving part and cooperatively retained by both parts. However, these conventional catheter connection hubs require proper positioning of the catheter receiving part relative to the fluid coupling part in order to receive and or secure the free end of the catheter thereto. Accordingly, it is desirable to provide a catheter connection hub that allows for robust assembly while minimizing the degree of uncertainty when making up a catheter with a connection hub.

BRIEF SUMMARY OF THE INVENTION

Fluid communication to an end of a catheter is afforded through a connection hub selectively attachable thereto. The connection hub includes a catheter-receiving element and a fluid-coupling element that are relatively rotatable coaxially between states by way of a determinant assembly feature in accordance with the invention. A first state is an "unlocked state" and second state is a "locked state." The unlocked state is for determinately receiving a catheter and the locked state is for determinately securing the catheter.

In certain embodiment of the invention a connection hub having a determinant assembly feature for attaching a catheter is provided. The connection hub includes a first body configured to slidably admit a free end of a catheter, and a second body configured to selectively effect fluid communication with the free end of the catheter when retentively attached thereto. The second body is rotatably secured to the first body for movement relative thereto between an unlocked state and a locked state.

In certain embodiments, a connection hub including a fluid-coupling element, a catheter-receiving element rotatably secured to the fluid-coupling element, and a determinant assembly feature restricting the rotational movement the fluid-coupling element relative to the catheter-receiving element between a catheter capture condition and a catheter receiving condition is provided.

In certain embodiments, a connection hub having a determinant assembly feature is provided. The connection hub includes a fluid-coupling element, a catheter-receiving element rotatably secured to the fluid-coupling element; and the determinant assembly feature restricting the rotational movement the fluid-coupling element relative to the catheter-receiving element between one of a locked state and an unlocked state.

A method of making a connection hub is also provided.

BRIEF DESCRIPTION OF THE DRAWINGS

FIG. 2 is a perspective view of the connection hub of FIG. 1 in the catheter capture condition thereof attached to the free end of the catheter of FIG. 1.

FIG. 3 is an enlarged fragmentary perspective view of the structures of the connection hub of FIG. 1 that latch the elements of the connection hub of FIGS. 1 and 2 in the catheter capture condition thereof shown in FIG. 2.

FIG. 4 is a transverse cross section of the connection hub of FIG. 2 taken along section line 4-4 therein, thereby depicting the structures illustrated in FIG. 3 interacting to latch the elements of the connection hub of FIGS. 1 and 2 in the catheter capture condition thereof shown in FIG. 2.

DETAILED DESCRIPTION OF THE INVENTION

The illustrations presented herein are, in some instances, not actual views of any particular connection hub, connection hub assembly or other feature of a connection hub assembly, but are merely idealized representations that are employed to describe the invention. Additionally, elements common between figures may retain the same numerical designation.

Figure 1:
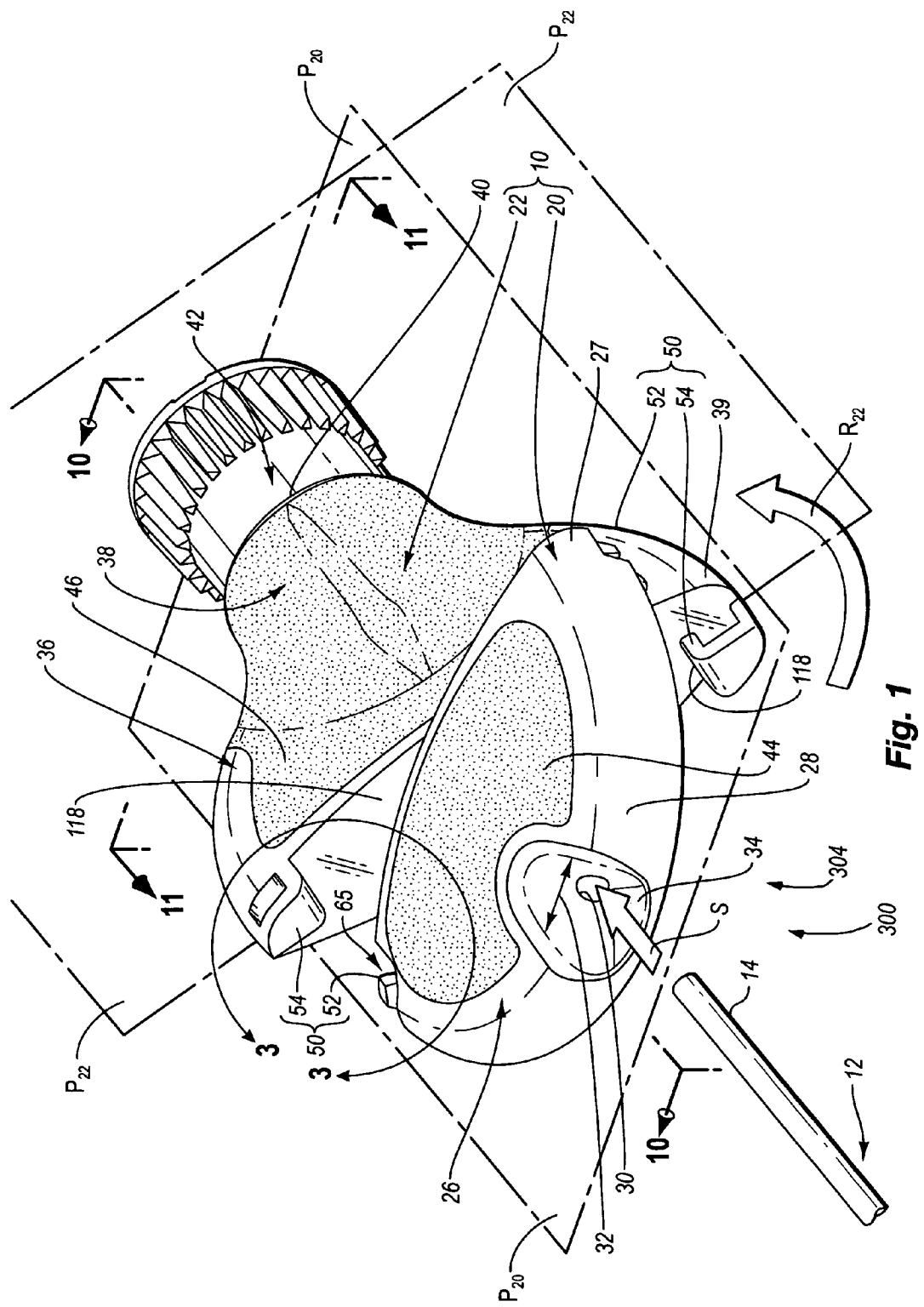
FIG. 1 is a perspective view of a connection hub embodying teachings of the invention shown in the catheter receiving condition thereof about to admit into the connection hub the free end of a catheter to be attached thereto.

In the following description, FIG. 1 shows a connection hub 10 embodying a determinant assembly feature 300 in accordance with the invention and a catheter 12. A free end 14 of the catheter 12 may be selectively attached to the hub 10 for enabling selective fluid communication to be effected with the interior of the catheter 12 from the free end 14 thereof. The components of the connection hub 10 apparent from the perspective view as shown in FIG. 1 include a catheter-receiving element 20 and a fluid-coupling element 22 that are secured in an abutting relationship so as to be capable of releasable engagement in coaxial rotation relative to each other. Such relative rotation R22 is indicated by an arrow in FIG. 1 that is oriented in the direction in which the fluid-coupling element 22 is to be rotated relative to the catheter-receiving element 20 in order to securely attach the catheter 12 to the connection hub 10 once the catheter 12 has been entered into the connection hub 10 in manner suggested by an arrow S, also shown in FIG. 1. Advantageously, the relative rotation R22 of the catheter-receiving element 20 and the fluid-coupling element 22 is determinately provided ensuring rotation between one of two states, i.e., a locked state 302 or an unlocked state 304, with the determinant assembly feature 300 (the elements of which are shown in FIGS. 5 through 8, 11 and 13) of the invention as described in detail below. As shown in FIG. 1, the connection hub 10 is in the unlocked state 304 for selectively receiving the catheter 12 in the catheter-receiving element 20 allowing retentive capture of the catheter 12 when the connection hub 10 is subsequently transitioned into the locked state 302 as ensured by the determinant assembly feature 300.

By way of overview, the connection hub 10 is described first and then the determinant assembly feature 300 will be described. Interior structures of the connection hub 10 are shown in FIGS. 5 through 13 that effect the rotational interconnection of the catheter-receiving element 20 and the fluid-coupling element 22 when securing the catheter 12. Other interior structures serve to attach the connection hub 10 to the catheter 12 by mechanically gripping the free end 14 of the catheter 12 and by establishing a fluid seal about the exterior thereof.

Nonetheless, the portion of the catheter-receiving element 20 visible in FIG. 1 takes the form of an actuation handle 26 for the catheter-receiving element 20. The actuation handle 26 has a generally planar external appearance that defines a plane P20 of the catheter-receiving element 20. In the embodiment depicted, the actuation handle 26 is a flattened semicircular disk, although alternative planar shapes in such an actuation handle would be consistent with the teachings of the invention. The actuation handle 26 has an abutment end 27 adjacent to the fluid-coupling element 22 and an outer end 28 remote therefrom that is configured to slidably admit the free end 14 of the catheter 12 into the connection hub 10. The entry of the free end 14 of the catheter 12 into the connection hub 10 occurs by way of an access opening 30 located at the narrowed terminus of a funnel shaped, open topped guideway 32 recessed into the outer end 28 of the actuation handle 26 on the side thereof visible in FIG. 1. The guideway 32 thus has a wedge shaped floor 34 that is parallel to the plane P20 of the catheter-receiving element 20. This configuration in the guideway 32 enables medical personnel to insert the free end 14 of the catheter 12 into the connection hub 10 without having to view the access opening 30 within the plane P20 of the catheter-receiving element 20.

The portion of the fluid-coupling element 22 visible in FIG. 1 takes the form of an actuation handle 36 for the fluid-coupling element 22. The actuation handle 36 has a generally planar external appearance that defines a plane P22 of the fluid-coupling element 22. In the embodiment depicted, the actuation handle 36 is a flattened semicircular disk, although alternative planar shapes in such an actuation handle would be consistent with the teachings of the invention. The fluid-coupling element 22 has an abutment end 39 adjacent to the catheter-receiving element 20 and remotely therefrom an outer end 40 configured to effect selective fluid communication through the connection hub 10 with the free end of any catheter to which the connection hub 10 becomes attached. Toward that end, the fluid-coupling element 22 is provided at the outer end 40 with a neck 38 that extends radially outwardly from the actuation handle 36. The free end of the neck 38 is designed to allow selective fluid communication to be effected through the connection hub 10 with the free end of any catheter attached thereto. In FIG. 1, however, the free end of neck 38 is obscured by a cap 42 that has been threaded onto the free end of neck 38 to preclude such fluid communication.

In FIG. 1, the plane P22 of the fluid-coupling element 22 is in a noncoplanar relationship to the plane P20 of the catheter-receiving element 20. The degree of the nonalignment between the plane P22 of the fluid-coupling element 22 and the plane P20 of the catheter-receiving element 20 may, however, be reduced through rotation R22 of the fluid-coupling element 22 relative to the catheter-receiving element 20 in the direction indicated by the arrow associated with rotation R22. Such is the manipulation that occurs in order to selectively attach the connection hub 10 to the free end of a catheter that has been admitted through the access opening 30 into the connection hub 10. The planar exterior configuration of the catheter-receiving element 20 as the actuation handle 26 and the planar exterior configuration of the fluid-coupling element 22 as the actuation handle 36 facilitates such relative rotation between the catheter-receiving element 20 and the fluid-coupling element 22.

The catheter-receiving element 20 and the fluid-coupling element 22 may be comprised of a relatively hard, moldable plastic, such as ABS, polycarbonate, lexan, polyamide, nylon, polyethylene ("PE") or an ABS polycarbonate blend, for example, and without limitation. Such materials are easily formed in known manufacturing processes to produce articles of structurally rigid, but not brittle, constitution. Thin structures made of such materials can as well be made to exhibit desirable degrees of resilient deformability. Other materials may be utilized that exhibit the qualities associated with producing the connection hub 10 suitable for connection with a catheter.

The exterior surface of the actuation handle 26 of the catheter-receiving element 20 may be provided with one or more inlay regions 44 having contrasting material properties from those exhibited by the balance of the catheter-receiving element 20. Similarly, the exterior surface actuation handle 36 of the fluid-coupling element 22 may be provided with one or more inlay regions 46 made of a material having contrasting properties to those of the material of which the balance of the fluid-coupling element 22 is comprised. One material of which each of inlay regions 44, 46 may be comprised is a soft, skin compatible material, such as Krayton, thermoplastic rubber ("TPR"), styrene acrylonitrile ("SAN"), thermoplastic elastomer ("TPE"), thermoplastic polyurethane ("TPU"), or Santoprene. The use of such soft materials in areas, such as inlay regions 44, 46, on exterior surfaces of elements of the connection hub 10, contributes positively to the purchase made available to medical personnel in manipulating the actuation handle 26 of the catheter-receiving element 20 and the actuation handle 36 of the fluid-coupling element 22 to cause rotation R22 of the fluid-coupling element 22. Inlay regions 44, 46, also contribute to patient comfort when the connection hub 10 is rested against the skin.

The abutting end 27 of the actuation handle 26 of the catheter-receiving element 20 and the abutting end 39 of the actuation handle 36 of the fluid-coupling element 22 are provided with the latches 50 that each include a paired hook 52 and an eye 54 that are located in an opposed relationship on respective of the catheter-receiving element 20 and the fluid-coupling element 22. Latches 50 limit the extent of relative rotation possible between the fluid-coupling element 22 and the catheter-receiving element 20. Latches 50 engage once rotation R22 of the fluid-coupling element 22 relative to the catheter-receiving element 20 has caused the connection hub 10 to become attached to the free end of a catheter, a condition that will hereinafter be referred to as the catheter capture condition, i.e., locked state 302, of the elements of the connection hub 10. Once engaged, latches 50 thus also preclude inadvertent dislodgement of the fluid-coupling element 22 and the catheter-receiving element 20 out of the catheter capture condition of the connection hub 10.

FIG. 2 depicts the catheter capture condition, or locked state 302 of the connection hub 10. There, the plane P22 of the fluid-coupling element 22 has been subjected to rotation R22 relative (shown in FIG. 1) to the catheter-receiving element 20 sufficient to be in a substantially coplanar relationship with the plane P20 of the catheter-receiving element 20. Correspondingly, the connection hub 10 takes on a generally planar appearance that defines a plane P10 of the connection hub 10 in the catheter capture condition thereof.

In FIG. 2, the cap 42 is shown threaded off the free end of the neck 38 of the fluid-coupling element 22. Revealed, as a result, on the free end of the neck 38 is a standard luer type connector 58 by which it is possible to place auxiliary medical equipment in fluid communication with the catheter 12 through the connection hub 10. In the catheter capture condition of the connection hub 10, the abutment end 27 of the actuation handle 26 of catheter the receiving element 20 is in congruent face-to-face engagement with the abutment end 39 of the actuation handle 36 of the fluid-coupling element 22. The connection hub 10 takes on the external overall appearance of a circular disk with the neck 38 projecting radially therefrom. The catheter-receiving element 20 and the fluid-coupling element 22 are restrained from easy dislodgement from the catheter capture condition of the connection hub 10 by the interaction of hooks 52 and eyes 54 of latches 50. A typical set of the structures associated with each latch 50 is depicted with enhanced detail in FIGS. 3 and 4.

FIG. 3 corresponds to the catheter receiving condition, i.e., the unlocked state 304, of the connection hub 10 shown in FIG. 1. The hook 52 comprises a shaft 62 with a barb 64 housed in a recess 65 in the exterior of the actuation handle 26 of the catheter-receiving element 20. The eye 54 on the fluid-coupling element 22 encloses a capture surface 66 that is provided with a detent 68 complimentary in shape and location in the hook 52 to the barb 64 on the shaft 62. As the catheter-receiving element 20 and the fluid-coupling element 22 are rotated toward the catheter capture condition of the connection hub 10, the hook 52 enters the eye 54. The barb 64 bears along the capture surface 66, resiliently deforming the shaft 62 of the hook 52 away from the capture surface 66. Once the catheter-receiving element 20 and the fluid-coupling element 22 reach a coplanar orientation in the catheter capture condition of the connection hub 10, the barb 64 reaches the detent 68 and snaps resiliently thereinto. This relationship is depicted in cross section as shown in FIG. 4.

Latches 50 thus serve as stops to the relative rotation of the fluid-coupling element 22 and the catheter-receiving element 20, and latches 50 constrain these elements of the connection hub 10 from inadvertent dislodgement out of the catheter capture condition thereof.

Figure 5:
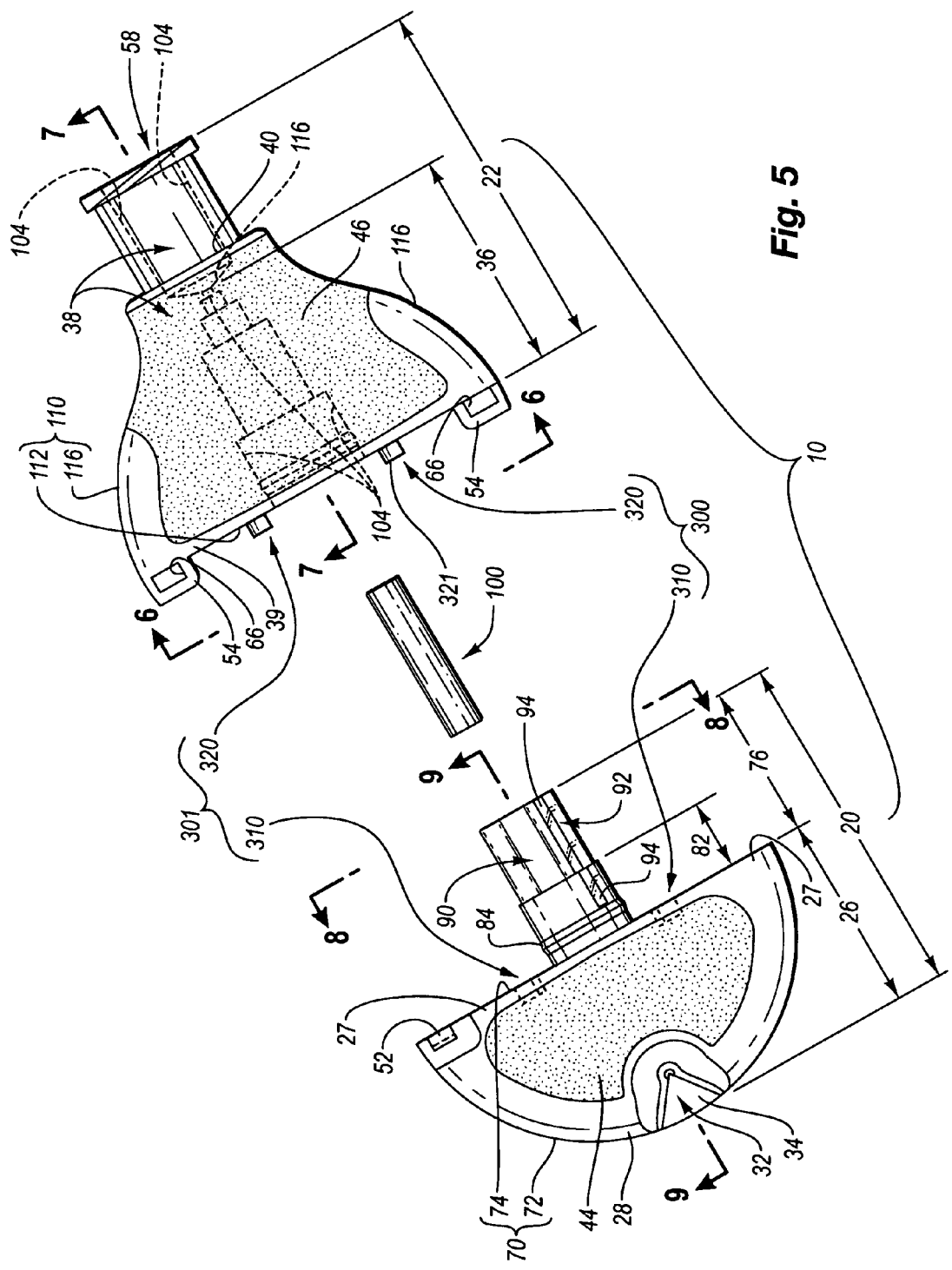
FIG. 5 is an exploded plan view of the connection hub of FIGS. 1 and 2.

FIG. 5 shows an exploded plan view of the connection hub 10. The actuation handle 26 of the catheter-receiving element 20 is shown in FIG. 5 to have a semicircular outer periphery 70 that includes an arcuate portion 72 that encompasses the outer end 28 of the actuation handle 26 and a linear diametrical portion 74 at the abutment end 27 thereof. Also revealed in FIG. 5 is a columnar structure 76 that projects normal to the abutment end 27 of the actuation handle 26 from a central location therealong. The base of the columnar structure 76 is a cylindrical axle 82 that is circumscribed at a medial position therealong by a continuous, raised retention ridge 84. The axle 82 and the retention ridge 84 in cooperation with corresponding structures internal to the fluid-coupling element 22 secure the catheter-receiving element 20 and the fluid-coupling element 22 in the relative rotational relationship that permits the transformation of the connection hub 10 of the catheter receiving condition thereof shown in FIG. 1 into the catheter capture condition thereof illustrated in FIG. 2.

Projecting from the axle 82 in alignment therewith are a first clamping jaw 90 and a second clamping jaw 92. Clamping jaws 90, 92 are separated by an elongated slot 94 that extends diametrically across the columnar structure 76 and longitudinally therethrough into the axle 83 to the retention ridge 84.

An additional element of the connection hub 10 first apparent in FIG. 5 is a tubular sealing sleeve 100. The sealing sleeve 100 may be comprised of synthetic polyisoprene, TPR, TPU, TPE, SAN, Santoprene, latex, or rubber, for example and without limitation. The sealing sleeve 100 of the connection hub 10 most intimately interacts with the free end of a catheter when attached to the connection hub 10. The sealing sleeve 100 is housed between the first clamping jaw 90 and the second clamping jaw 92, when the catheter-receiving element 20 and the fluid-coupling element 22 are assembled as in FIGS. 1 and 2. Under these circumstances, the axle 82, clamping jaws 90, 92, and the sealing sleeve 100 are entered into an interior space 104 of the fluid-coupling element 22 that is shown by hidden lines in FIG. 5.

In the plan view shown in FIG. 5, a periphery 110 of the actuation handle 36 of the fluid-coupling element 22 is generally semicircular in shape, including a linear diametrical portion 112 formed at the abutment end 39 of the fluid-coupling element 22 and an arcuate portion 116, as indicated in phantom, interrupted, at the outer end 40 of the actuation handle 36 of the fluid-coupling element 22, by the neck 38.

Figure 6:
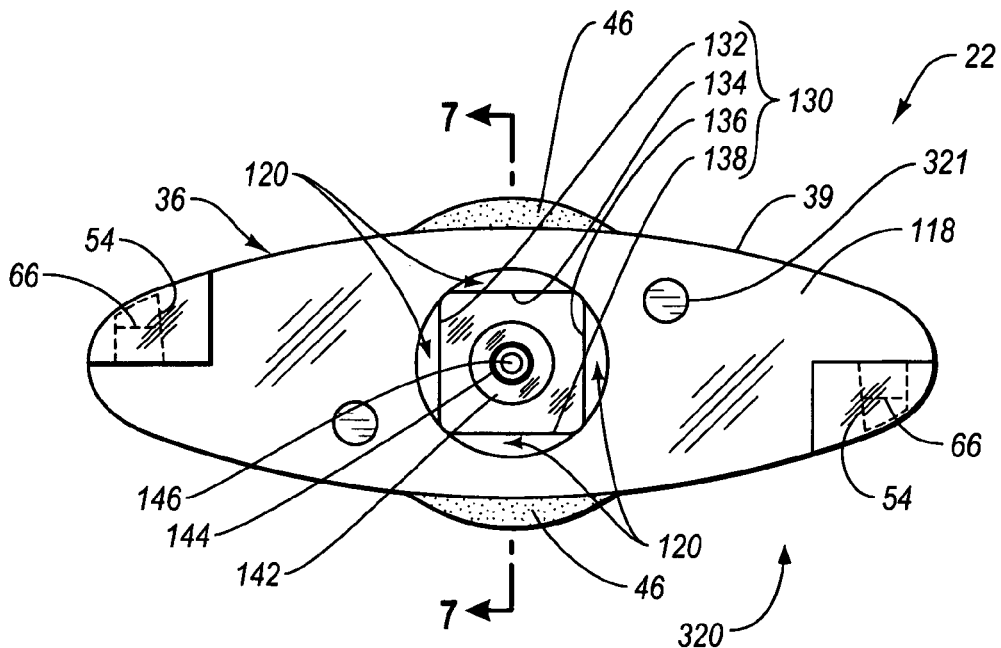
FIG. 6 is an end view of the fluid-coupling element of the connection hub of FIG. 5 taken from the perspective of line 6-6 therein.
Figure 7:
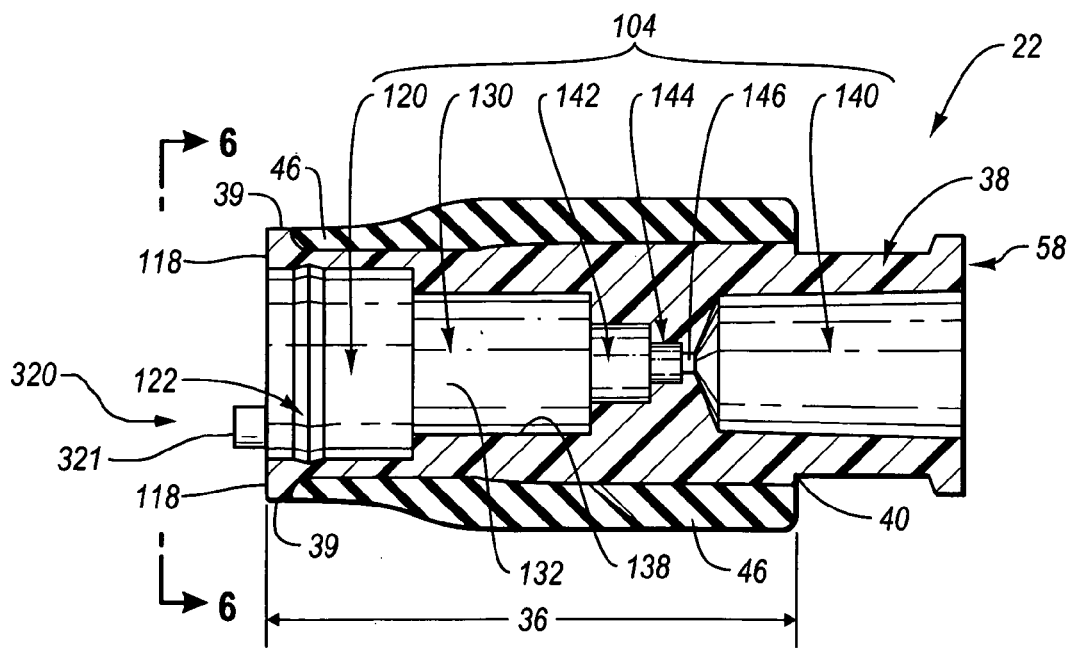
FIG. 7 is a longitudinal cross section of the fluid-coupling element shown in FIGS. 5 and 6 taken along section line 7-7 therein.

A better understanding of the interior space 104 in the fluid-coupling element 22 may be acquired by reference to FIGS. 6 and 7 taken together. There, it should first be appreciated that the diametrical portion 112 of the periphery 110 of the actuation handle 36 of the fluid-coupling element 22 corresponds to a planar interface surface 118 of the actuation handle 36 located at the abutment end 39 thereof. Opening centrally of the interface surface 118 is a cylindrical bore 120 that is encircled by a continuous retention groove 122. The bore 120 and the retention groove 122 are so sized as to enable the retention ridge 84 on the exterior of the axle 82 to be snappingly received into the retention groove 122, when the catheter-receiving element 20 and the fluid-coupling element 22 are assembled into abutment as shown in FIGS. 1 and 2.

Opening to the exterior of the fluid-coupling element 22 through the bore 120 is a clamp actuation socket 130 that is bounded by perpendicular walls 132, 134, 136, 138, of equal length. Thus, the clamp actuation socket 130 is possessed of a transverse cross sectional shape shown to best advantage in FIG. 6 as being square.

The end of the clamp actuation socket 130 opposite from the bore 120 communicates through a series of three coaxially disposed spaces of reducing diameter toward an interior 140 of the luer type connector 58. Moving from the clamp actuation socket 130 toward the interior 140 of the luer type connector 58, these cylindrical spaces include, first a sealing sleeve abutment chamber 142, second a smaller catheter abutment chamber 144, and lastly, a diminutive fluid passageway 146 calculated to afford fluid communication from the interior 140 of the luer type connector 58 to the interior of the free end of any catheter lodged in the catheter abutment chamber 144.

Figure 8:
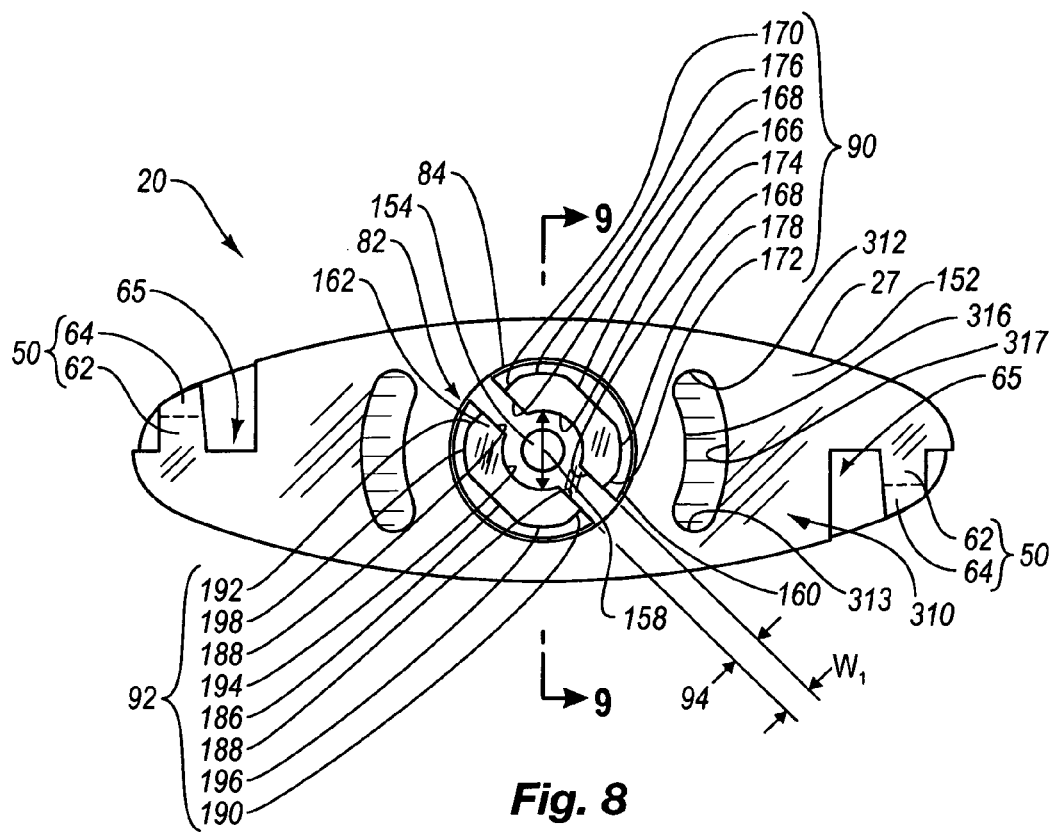
FIG. 8 is an end view of the catheter-receiving element of the connection hub of FIG. 5 taken from the perspective of line 8-8 therein.
Figure 9:
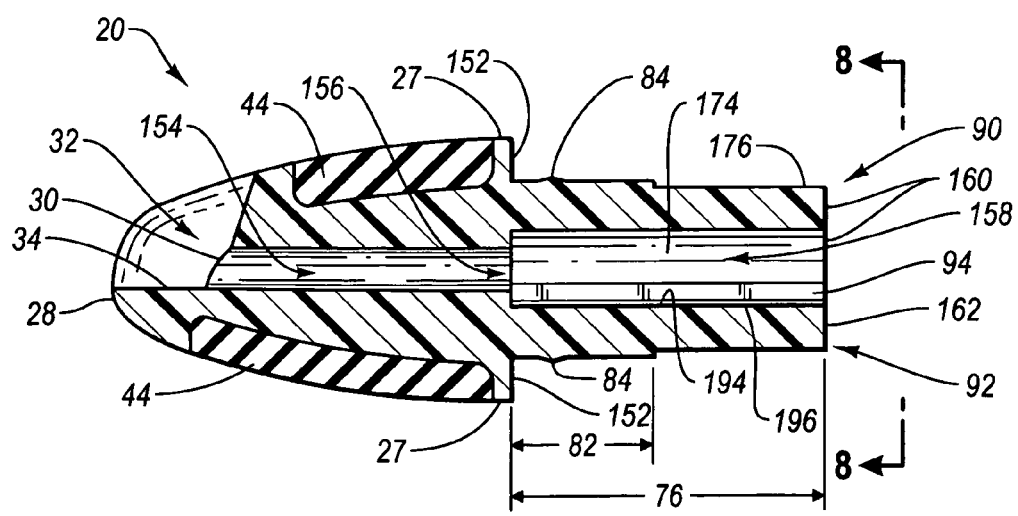
FIG. 9 is a longitudinal cross section of the catheter-receiving element of FIGS. 5 and 8 taken along section line 9-9 therein.

An understanding of the columnar structure 76 projecting from the abutment end 118 of the actuation handle 26 can be acquired by reference to FIGS. 8 and 9 taken together. There, it should first be appreciated that the diametrical portion 74 of the periphery 70 of the actuation handle 26 corresponds to a planar interface surface 152 from which the columnar structure 76 projects centrally. Formed centrally through the actuation handle 26 of the catheter-receiving element 20 is a catheter passageway 154 that extends from the access opening 30 at the outer end 28 of the actuation handle 26 to an inner opening 156 at the abutment end 27 thereof. At the inner opening 156, the catheter passageway 154 opens into larger sealing sleeve receiving chamber 158 that extends centrally through the full length of the columnar structure 76, sharing in part space interior of the columnar structure 76 identified earlier as comprising the slot 94 between clamping jaws 90, 92.

In the assembled condition of connection hub 10 illustrated in FIGS. 1 and 2, the end of the sealing sleeve 100 remote from the catheter abutment chamber 144 is disposed directly facing the inner opening 156 to the catheter passageway 154 in the actuation handle 26 of the catheter-receiving element 22. The sealing sleeve 100, the receiving chamber 158, and the catheter abutment chamber 144 are so sized as to accommodate the full length of the sealing sleeve 100 and so oriented mutually as to align the interior passageway in the sealing sleeve 100 between the catheter passageway 154 in the actuation handle 26 and catheter abutment chamber 144 of the interior space 104 in fluid-coupling element 22.

As a consequence of these relationships in the columnar structure 176, clamping jaws 90, 92, can be understood to project from the abutment end 27 of the actuation handle 26 on opposite sides of the inner opening 156 to the catheter passageway 154. Clamping jaws 90, 92, terminate at equal distances from the abutment end 27 of actuation handle 26. The first clamping jaw 90 thus terminates in a first clamp tip 160, and the second clamp jaw 92 terminates in a second clamp tip 162.

In FIG. 8, the first clamping jaw 90 is an elongated, planar structure bounded by a wide, flat outer surface 166 and a parallel, flat inner clamp surface 168. The outer surface 166 and the clamp surface 168 are connected at the ends thereof by respective shorter side surfaces 170, 172. The clamp surface 168 of the first clamping jaw 90 thus defines one side of the slot 94 in the columnar structure 76 between clamping jaws 90, 92.

The positioning of the sealing sleeve receiving chamber 158 centrally of the columnar structure 76 in a space shared with the slot 94, in combination with a diameter in the sealing sleeve receiving chamber 158 that is larger than the width W1 of the slot 94 shown in FIGS. 8 and 9, results in the clamp surface 168 of the first clamping jaw 90 being traversed centrally by a longitudinally extending, open ended catheter accommodation recess 174 of semicircular cross section. The catheter accommodation recess 174 is aligned with the inner opening 156 to the catheter passageway 154 when, as in FIGS. 8 and 9, the first clamping jaw 90 is free from the influence of external forces. In the embodiment illustrated, the transverse cross sectional configuration of the first clamping jaw 90 is invariant along the full length thereof.

Significantly, relative to the action of the first clamping jaw 90 in attaching the connection hub 10 to the free end of a catheter, the outer surface 166 of the first clamping jaw 90 and the end surface 170 thereof are interconnected in a smooth, tangential manner by a curved bearing surface 176. Similarly, the outer surface 166 of the first clamping jaw 90 and the end surface 172 thereof are interconnected in a smooth, tangential manner by a curved bearing surface 178.

The second clamping jaw 92 is structured identically to the first clamping jaw 90. Thus, the first clamping jaw 90 is an elongated, planar structure bounded by a wide, flat outer surface 186 and a parallel, flat inner clamp surface 188. The outer surface 186 and the clamp surface 188 are connected at the ends thereof by respective shorter side surfaces 190, 192. The inner clamp surface 198 of the second clamping jaw 92 thus defines one side of the slot 94 in the columnar structure 96 between clamping jaws 90, 92.

The positioning of the sealing sleeve receiving chamber 158 centrally of the columnar structure 76 in a space shared with the slot 94, in combination with a diameter in the sealing sleeve receiving chamber 158 that is larger than the width WI of the slot 94 shown in FIGS. 8 and 9, results in the clamp surface 188 of the first clamping jaw 90 being traversed centrally by a longitudinally extending, open ended catheter accommodation recess 194 of semicircular cross section. The catheter accommodation recess 194 is aligned with the inner opening 156 to the catheter passageway 174 when, as in FIGS. 8 and 9, the second clamping jaw 92 is free from the influence of external forces. In the embodiment illustrated, the transverse cross sectional configuration of the second clamping jaw 92 is invariant along the full length thereof.

Significantly, relative to the action of the second clamping jaw 92 in attaching the connection hub 10 to the free end of a catheter, the outer surface 186 of the second clamping jaw 92 and the end surface 190 thereof are interconnected in a smooth, tangential manner by a curved bearing surface 196. Similarly, the outer surface 186 of the second clamping jaw 92 and the end surface 192 thereof are interconnected in a smooth, tangential manner by a curved bearing surface 198. The free end 14 of the catheter 12 has been slid through the catheter passageway 154 in the catheter-receiving element 20, through the full length of the sealing sleeve 100, and into the catheter abutment chamber 144.

Figure 10:
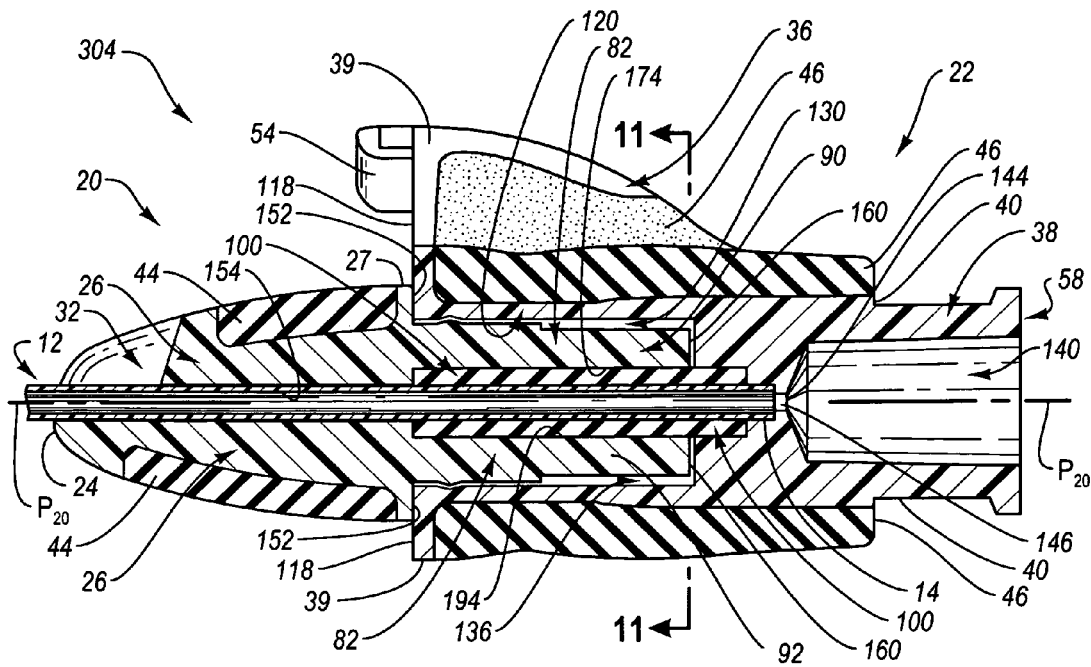
FIG. 10 is a longitudinal cross section of the connection hub of FIG. 1 taken along section line 10-10 therein, thereby to illustrate the interaction of internal structures of the elements of the connection hub in the catheter receiving condition thereof.
Figure 11:
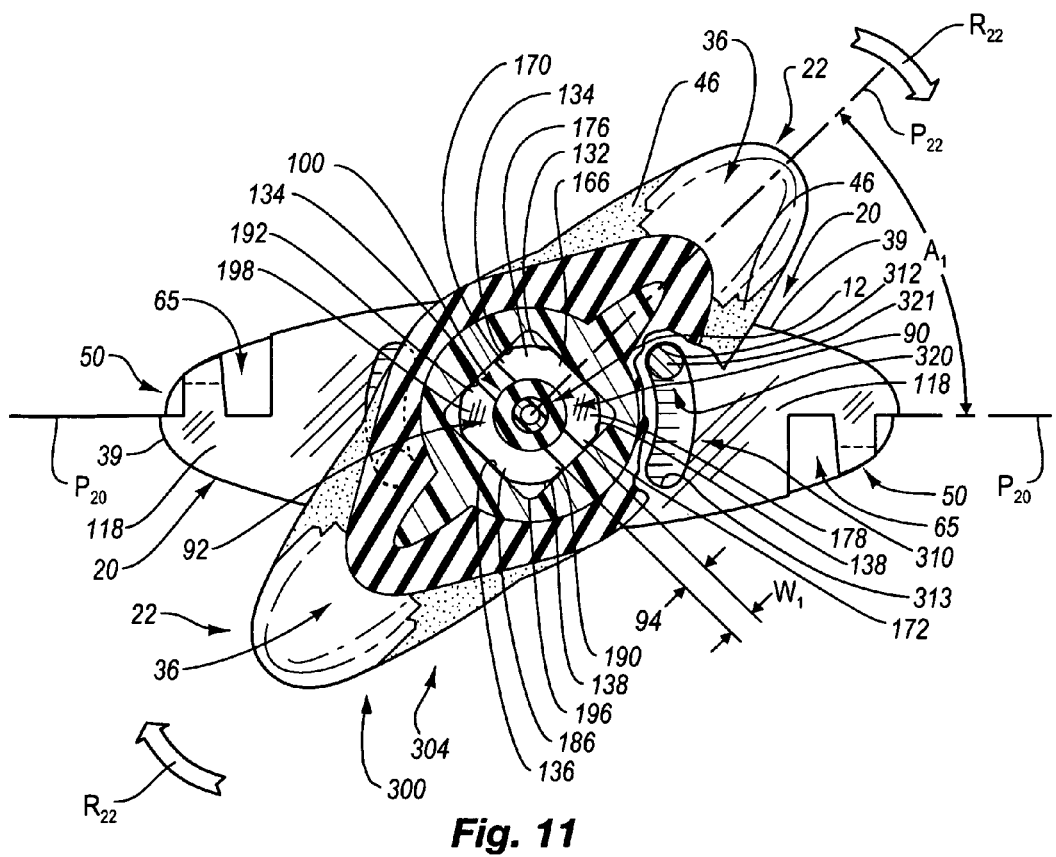
FIG. 11 is a transverse cross section of the connection hub of FIG. 1 taken along section line 11-11 therein at a location more clearly appreciated from the inclusion of section line 11-11 also in FIG. 10, and includes a cutaway perspective of the inventive details.

FIGS. 10 and 11 show cross sections of the elements of connection hub 10 in the catheter receiving condition, i.e., the unlocked state 304, thereof illustrated in FIG. 1. In FIG. 10, the interface surface 152 at the abutment end 27 of the actuation handle 26 of the catheter-receiving element 20 is in engagement with the interface surface 118 at the abutment end 39 of the engagement handle 36 of the fluid-coupling element 22. The first and second clamping jaws 90, 92, with the sealing sleeve 100 therebetween, are received in the clamp actuation socket 130 interior of the fluid-coupling element 22.

The fluid-coupling element 22 is capable of rotation R22 relative to the catheter-receiving element 20 as indicated in FIG. 11 by arrows. Prior to any such rotation, however, plane P22 of the fluid-coupling element 22 is disposed at an acute angle A1 of about 45° relative to plane P20 of the catheter-receiving element 20. Clamping jaws 90, 92 are in an open condition thereof with the slot 94 therebetween being of undiminished width W1. The wall 132 of the clamp actuation socket 130 opposes the outer surface 66 of the first clamping jaw 90, and the wall 136 of the clamp actuation socket 130 opposes the outer surface 86 of the second clamping jaw 92. The wall 134 of the clamp actuation socket 130 opposes the side surface 170 of the first clamping jaw 90, the side surface 192 of the second clamping jaw 92, and an entry into the slot 94 located therebetween. The wall 138 of the clamp actuation socket 130 opposes the side surface 172 of the first clamping jaw 90, the side surface 190 of the second clamping jaw 92, and an opening into the slot 94 located therebetween.

Figure 11A:
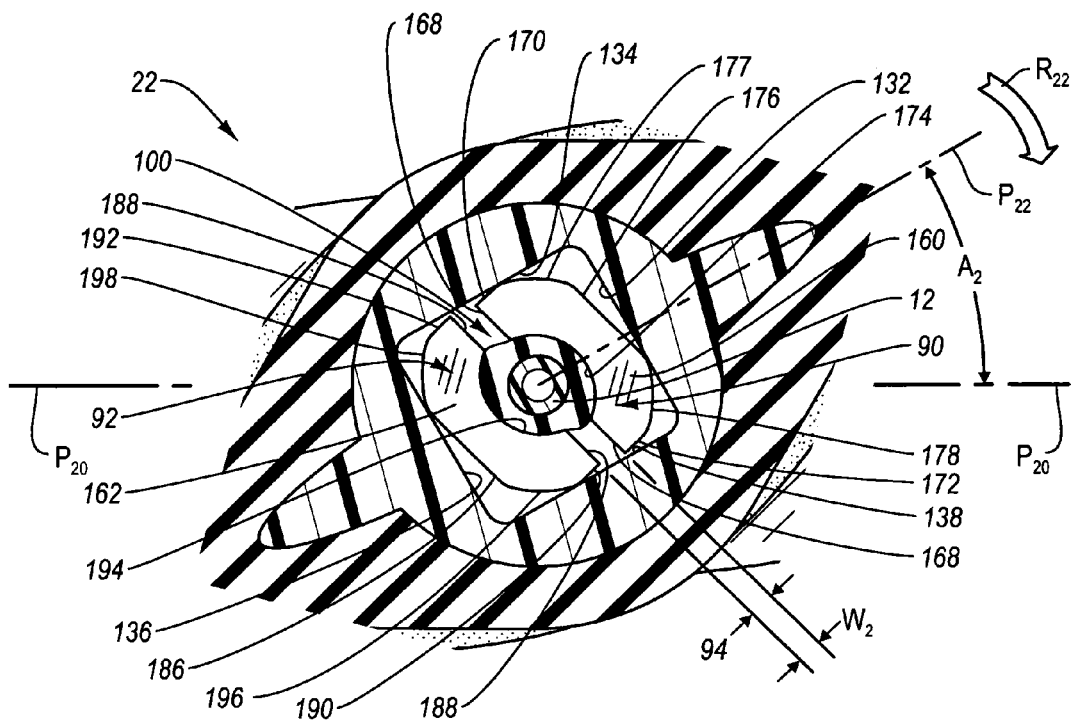
FIGS. 11A and 11B are a sequence of transverse cross sections of internal structures of the catheter receiving condition of the connection hub of FIG. 10 and 11 undergoing progressively increased relative rotation into the catheter capture condition of the connection hub as illustrated in FIGS. 12 and 13.
Figure 11B:
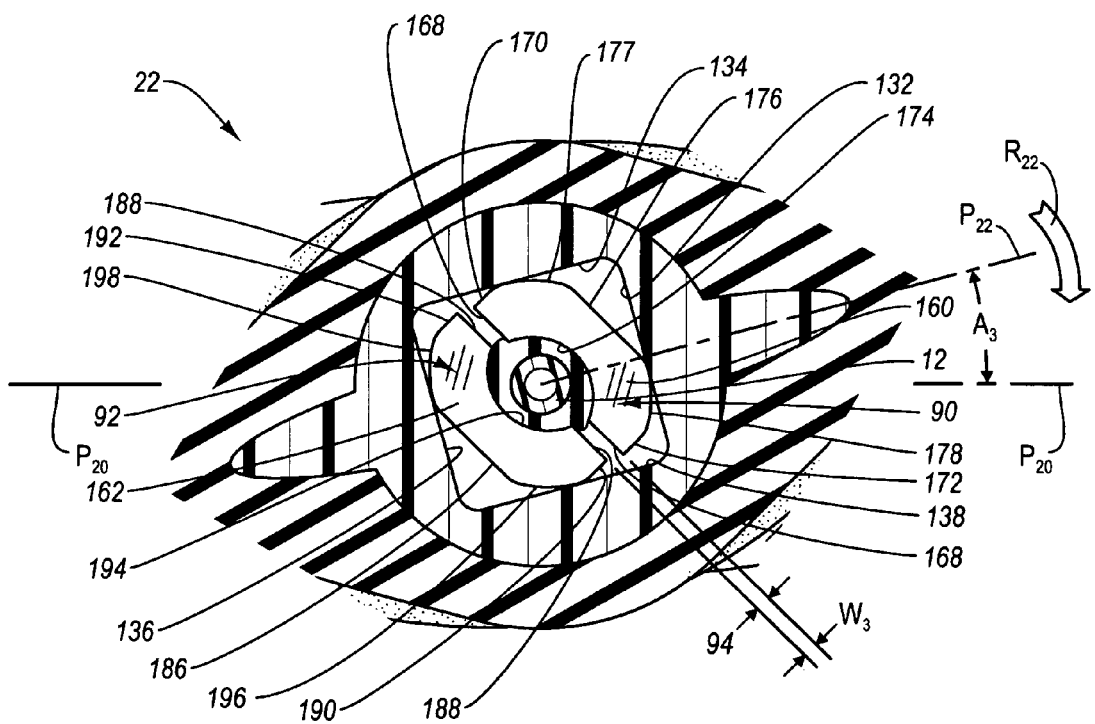

FIGS. 11A and 11B are a sequence of enlarged transverse cross sectional views of the central portion of FIG. 11 illustrating relative assumed positions by elements of the clamp actuation socket 30 and clamping jaws 90, 92, during progressive rotation R22 of the fluid-coupling element 22 relative to the catheter-receiving element 20.

Plane P20 of the catheter-receiving element 20 is shown in each of FIGS. 11A and 11B, whereby it is to be understood that the catheter-receiving element 20 and all components thereof, such as clamping jaws 90, 92, remain in the same orientation as shown in FIG. 11, while being an interior feature of the fluid-coupling element 22, the clamp actuation socket 130 engages in coaxial rotation R22 relative thereto. The relative rotation of the clamp actuation socket 130 illustrated in the sequence of FIGS. 11A and 11B serves to progressively urge the first clamping jaw 90 into ever closer proximity to the second clamping jaw 92, compressing the sealing sleeve 100 about a free end 14 of a catheter 12 in the process.

In FIG. 11A, plane P22 of the fluid-coupling element 22 has been caused to engage in rotation R22 relative to the catheter-receiving element 20 from the position illustrated in FIG. 11 by about 15°. As a result, the angle A2 between plane P22 of the fluid-coupling element 22 and plane P20 of the catheter-receiving element 20 is only approximately 30°. Components of the catheter-receiving element 20, such as clamping jaws 90, 92, as well as the sealing sleeve 100 disposed therebetween, remained stationary in that process, but the clamp actuation socket 130 rotated approximately 15° relative thereto. As a result, the side 134 of the actuation socket 130 has commenced to ride over the bearing surface 176 on the first clamping jaw 90, and the side 166 of the clamp actuation socket 130 has commenced to ride over the bearing surface 178 of the first clamping jaw 190. Such relative movement between interior surfaces of the clamp actuation socket 130 and the exterior of the first clamping jaw 90 is accommodated as a result of planar cross sectional configuration of the first clamping jaw 90 by a radially inward resilient deformation of the first clamping jaw 90 toward the second clamping jaw 92. Similarly, the wall 138 of the clamp actuation socket 30 has commenced to ride over the bearing surface 96 of the second clamping jaw 92, while the wall 36 of the clamp actuation socket 30 has commenced to ride over the bearing surface 98 of the second clamping jaw 92. These relative movements between the interior of the clamp actuation socket 30 and the exterior of the second clamping jaw 92 urge the clamping jaw 92 resiliently radially inwardly toward the first clamping jaw 90, accommodated in that process by the planar cross sectional configuration of the second clamping jaw 92.

In FIG. 11B, plane P22 of the fluid-coupling element 22 has been caused to engage in rotation R22 relative to the catheter-receiving element 20 from the position illustrated in FIG. 11A by about 15°. As a result, the angle A2 between plane P22 of the fluid-coupling element 22 and plane P20 of the catheter-receiving element 20 is only approximately 30°. Components of the catheter-receiving element 20, such as clamping jaws 90, 92, as well as the sealing sleeve 100 disposed therebetween, remained stationary in that process, but the clamp actuation socket 130 rotated approximately another 15° relative thereto. As a result, the side 134 of the actuation socket 130 has ridden further over the bearing surface 176 on the first clamping jaw 90, and the side 166 of the clamp actuation socket 130 has ridden further over the bearing surface 178 of the first clamping jaw 190. Such relative movement between interior surfaces of the clamp actuation socket 130 and the exterior of the first clamping jaw 90 is accommodated as a result of planar cross sectional configuration of the first clamping jaw 90 by a radially inward resilient deformation of the first clamping jaw 90 toward the second clamping jaw 92. Similarly, the wall 138 of the clamp actuation socket 30 has ridden further over the bearing surface 96 of the second clamping jaw 92, while the wall 36 of the clamp actuation socket 30 has ridden further over the bearing surface 98 of the second clamping jaw 92. These relative movements between the interior of the clamp actuation socket 30 and the exterior of the second clamping jaw 92 urge the clamping jaw 92 resiliently radially inwardly toward the first clamping jaw 90, accommodated in that process by the planar cross sectional configuration of the second clamping jaw 92.

Further rotation of the fluid-coupling element 22 relative to the catheter-receiving element 20 brings plane P22 of the fluid-coupling element 22 by another 15° into coplanar alignment with plane P20 of the catheter-receiving element 20 into the catheter capture condition or locked state 302 of the connection hub 10 shown in FIG. 2. The catheter capture condition of connection hub 10 is further illuminated through the cross sectional views provided in FIGS. 12 and 13.

Figure 13:
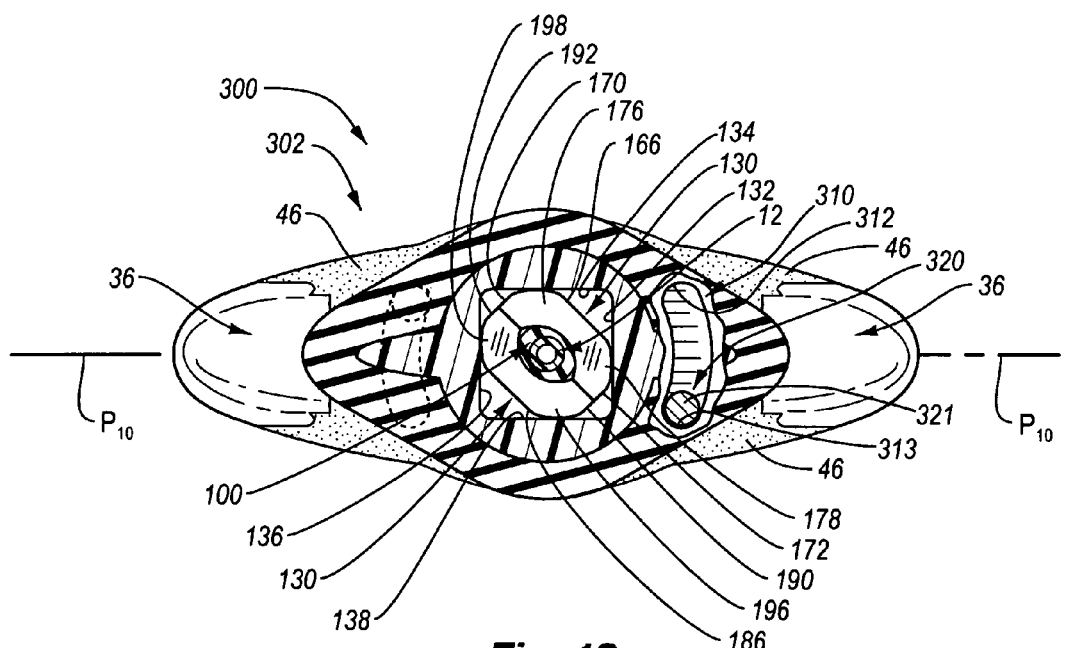
FIG. 13 is a transverse cross section of the connection hub of FIG. 2 taken along section line 11-11 therein at a location more clearly appreciated from the inclusion of section line 13-13 also in FIG. 12, and includes a cutaway perspective of the inventive details.

As shown in FIG. 13, the rotation of the clamp actuation socket 130 relative to clamping jaws 90, 92 has produced sufficient resilient deformation of clamping jaws 90, 92 radially toward each other as to bring clamping jaws 90, 92 into closed condition thereof. The clamp surface 168 of the first clamping jaw 90 abuts the clamp surface 188 of the second clamping jaw 192. As a result, the sealing sleeve 100 is intensely compressed within the catheter accommodation recess 174 and the catheter accommodation recess 194 that have been brought into aligned opposition by a resilient radially inward deformation of clamping jaws 90, 92. Thus, in the closed condition of clamping jaws 90, 92, the free end 14 of the catheter 12 is gripped mechanically through the sealing sleeve 100 by catheter accommodation recesses 174, 194, and the sealing sleeve 100 is urged by clamping jaws 90, 92, into a fluid seal about the exterior of the free end 14 of the catheter 12.

Figure 12:
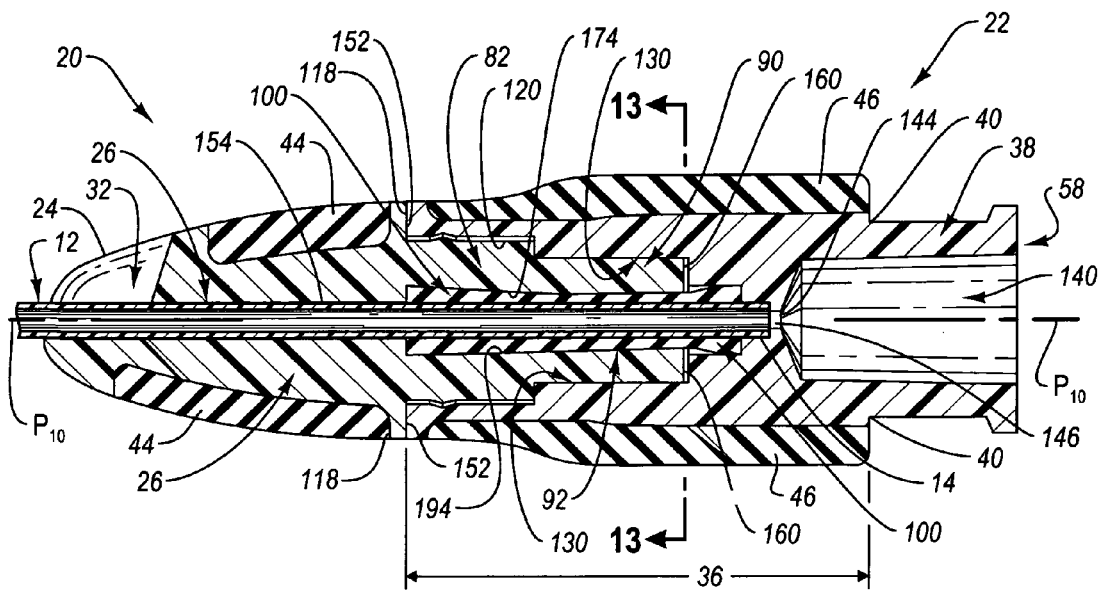
FIG. 12 is a longitudinal cross section of the connection hub of FIG. 2 taken along section line 12-12 therein, thereby to illustrate the interaction of internal structures of the elements of the connection hub in the catheter capture condition thereof.

As shown in FIG. 12, the force exerted on the exterior of the free end 14 of the catheter 12 by clamping jaws 90, 92, is focused longitudinally along the tube of the catheter 12 at a location between the first clamp tip 160 of the first clamping jaw 90 and the second clamp tip 162 of the second clamping jaw 192. The force of the mechanical grip exercised on the catheter 12 in this manner is thus advantageously controllable through the design of the clamp actuation socket 30 and the cross sectional configurations of clamping jaws 90, 92.

Other embodiments are contemplated for retentively receiving a catheter in a catheter connection hub. For example, embodiments for retentively receiving and securing a catheter in a catheter connection hub are provided for in PCT International Publication Number WO/2006/099306 A2, published Sep. 21, 2006, titled "Catheter Connection Hub," the contents of which in its entirety are incorporated herein by this reference.

Turning now to the inventive details of the determinant assembly feature 300, attention is again directed to FIG. 5. The determinant assembly feature 300 comprises, when the portions of the connection hub 10 are cooperatively engaged as shown in FIG. 1, a rotational engagement element, or recess, 310 and a rotational stop element, or extension, 320. The rotational engagement element 310 (shown with hidden lines) extends into the linear diametrical portion 74 at the abutment end 27 of the catheter-receiving element 20. The rotational stop element 320 projects normal to the linear diametrical portion 112 at the abutment end 39 of the fluid-coupling element 22. The rotational stop element 320 engages the rotational engagement element 310 as the axle 82 and the retention ridge 84 in cooperation with corresponding structures internal to the fluid-coupling element 22 secure the catheter-receiving element 20 and the fluid-coupling element 22 together in the catheter receiving condition or unlocked state 304, as shown in FIG. 1. Also provided in this embodiment of the invention is another determinant assembly feature 301 that is optionally symmetrically positioned 180 degrees rotationally with respect to the determinant assembly feature 300 and having common elements as described hereinafter.

As will be appreciated and described in further detail below, the determinant assembly feature 300 permits the transformation of the connection hub 10 in the catheter receiving condition, or unlocked state, 304 shown in FIG. 1 to rotate about 45 degrees into the catheter capture condition, or locked state, 302 as illustrated in FIG. 2, while assuredly preventing rotation into an indeterminate state such as by rotating in the opposite direction from rotation R22, as described hereinabove. Conventional connection hubs may allow for rotation in either direction potentially causing additional delay when connecting-up a catheter with the connection hub. Advantageously, a skilled or unskilled worker will have positive knowledge as to when the connection hub 10 is in the catheter receiving condition or unlocked state 304 allowing for easy insertion of a catheter 12 therein, and when the connection hub 10 is in the catheter capture condition or locked state 302. In the locked state 302, the determinant assembly feature 300 advantageously prevents improper insertion of a catheter 12 or securely retains a properly received catheter 12, therein, respectively. In this respect, when the connection hub 10 is located in the locked state 302 by the hook 52 and eye 54 of latches 50, a catheter 12 may not be inserted or removed from reception with sealing sleeve 100 and compressed by clamping jaws 90, 92. In like fashion, when the connection hub 10 is located in the unlocked state 304, a catheter 12 may be freely inserted into the sealing sleeve 100 for later compression and retention properly between clamping jaws 90 and 92 as it is transitioned into the locked state 302. Accordingly, the determinant assembly feature 300 provides assurance of transitioning between only two states 302 and 304, making for robust connection between a catheter 12 and the connection hub 10.

The rotational stop element, or extension, 320 is also shown in FIGS. 6 and 7, and is a cylindrical stub 321 extending normal from the planar interface surface 118 of the fluid-coupling element 22 and is suitable for rotational engagement with the rotational engagement element 310 as described herein. It is recognized that while the rotational stop element 320 is the cylindrical stub 321, it may have other shapes consistent with the disclosure herein provided for allowing determinant rotational positioning of the elements of the connection hub 10 for receiving and retaining a catheter.

The rotational engagement element, or recess, 310 is also shown in FIG. 8, and is a channel 311 extending into the planar interface surface 152 of the catheter-receiving element 20 having a crescent or arcuate shaped sidewalls 316, 317 and end stops 312, 313. The arcuate shaped sidewalls 316, 317 extend substantially in a circumferential direction following the rotational path dictated by the coaxial rotation of the catheter-receiving element 20 and the fluid-coupling element 22 of the connection hub 10. The sidewalls 316, 317 are separated by a sufficient radial distance to allow the rotational stop element 320 to move freely therebetween upon transition between either state 302 or 304. Each end stop 312 and 313 limit the motion of the rotational stop element 320 beyond the unlocked state 304 or the locked state 302 in respective directions, respectively, by arresting the undesired rotation of the catheter-receiving element 20 relative to the fluid-coupling element 22. It is recognized that while the rotational engagement element 310 is a crescent shaped channel 311, it may have other shapes consistent with the disclosure herein provided for allowing determinant rotational positioning of the elements of the connection hub 10 for receiving and retaining a catheter.

While the rotational engagement element 310 and the rotational stop element 320 of the determinant assembly feature 300 are shown, respectively, on the catheter-receiving element 20 and the fluid coupling element 22, each feature 310 and 320 may be on opposite elements 22 and 20, respectively. Moreover, the rotational stop element 320 and the rotational engagement element 310 may be configured with other structural features than the channel 311 or the stub 321, as illustrated.

The interaction of the rotational engagement element 310 and the rotational stop element 320 of the determinant assembly feature 300 is illustrated in the cutaway perspective shown in FIG. 11 and 13.

In FIG. 11, the rotational engagement element 310 is shown engaging the rotational stop element 320 in the unlocked state 304 with the plane P22 of the fluid-coupling element 22 in a noncoplanar relationship to the plane P20 of the catheter-receiving element 20. As mentioned hereinabove, the degree of the nonalignment between the plane P22 of the fluid-coupling element 22 and the plane P20 of the catheter-receiving element 20 may, however, be reduced through rotation R22 of the fluid-coupling element 22 relative to the catheter-receiving element 20 in the direction indicated by the arrow associated with rotation R22. By way of the determinate assembly feature 300, however, the nonalignment between the plane P22 of the fluid-coupling element 22 and the plane P20 of the catheter-receiving element 20 may not transition in the opposite direction indicated by the arrow associated with rotation R22. In this respect, the end stop 312 of the rotational engagement element 310 arrests undesired opposite rotational motion of stub 321 of the rotational stop element 320 when the catheter-receiving element 20 and the fluid-coupling element 22 are in abutting relationship in the unlocked state 304, thereby also affording a positive indication to a medical technician, nurse or doctor that a catheter 12 may now be received or removed from the connection hub 10.

As an additional observation, the non-coplanar relationship between the plane P20 and the plane P22 when in the unlocked state 304 is about 45 degrees, which corresponds with the non-engagement of the clamp actuation socket 130 with clamping jaws 90, 92. Conversely, the locked state 302 occurs when there is about 0 degrees separating the planes P20 and P22, i.e., substantially coplanar in alignment, which corresponds with the full engagement of the clamp actuation socket 130 with clamping jaws 90, 92 when compressing the sealing sleeve 100, as illustrated in FIG. 13. One of skill in the art would recognize that the relative orientation or non-coplanar relationship between plans P20 and P22 may be varied to a greater or lesser extent than the 45 rotational degrees shown.

In FIG. 13, the rotational engagement element 310 is shown engaging the rotational stop element 320 in the locked state 302 with the plane P22 of the fluid-coupling element 22 in a coplanar relationship to the plane P20 of the catheter-receiving element 20. By way of the determinate assembly feature 300, the alignment between the plane P22 of the fluid-coupling element 22 and the plane P20 of the catheter-receiving element 20 may not transition beyond the locked state 302 in the direction indicated by the arrow associated with rotation R22 mentioned hereinabove. In this respect, the end stop 313 of the rotational engagement element 310 arrests undesired rotational motion of stub 321 of the rotational stop element 320 when the catheter-receiving element 20 and the fluid-coupling element 22 are in abutting relationship in the locked state 302, thereby also affording a positive indication to a medical technician, nurse or doctor that a catheter 12 may not be received into or removed from the connection hub 10.

It is recognized that while the latches 50, e.g., the hook 52 and eye 54, may provide some of the functionality as herein described above as attributed with the locked state 302 determinant assembly feature 300, the latches 50 may be configured with other structural configurations not structurally consistent in meeting with the requirements of the invention, and may, however, be used for satisfying at least a portion of the determinant assembly feature 300 as herein described.

In yet another embodiment of the invention, the determinant assembly feature 300 allows for axial connection of the catheter-receiving element 20 and the fluid-coupling element 22 together while oriented in the to be received, when connected, condition (i.e., the unlocked state 304), and, after connection, allows for determinate positioning rotationally between the unlocked state 304 and the locked state 302. In yet another aspect, the catheter-receiving element 20 and the fluid-coupling element 22 may not be axially uncoupled when in the locked state 302.

After having been apprised of the disclosure hereof, one of ordinary skill in the art would be able to make and use the invention, in further manners and means.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A connection hub having a determinant assembly feature for attaching a catheter, the connection hub comprising:
    a catheter-receiving element configured to slidably admit a free end of a catheter, the catheter-receiving element comprising:
        a catheter-receiving element actuation handle, comprising:
            an outer end configured to slidably admit the free end of the catheter into the connection hub;
            an abutment end opposite the outer end; and
            a catheter passageway extending through the catheter-receiving element actuation handle between an access opening at the outer end thereof and an inner opening at the abutment end thereof;
        a pair of resilient elongated, parallel clamping jaws projecting from the abutment end of the catheter-receiving element actuation handle on opposite sides of the inner opening to the catheter passageway, each of the clamping jaws terminating equidistant from the abutment end of the catheter-receiving element actuation handle in a respective clamp tip and an associated inner clamp-tip surface centrally traversed by an open-ended catheter accommodation recess aligned with the inner opening to the catheter passageway, the clamping jaws assuming an open condition thereof when free from the influence of external forces and a closed condition thereof when under the influence of external forces, in the open condition of the clamping jaws the inner clamp-tip surfaces on the clamping jaws being in a substantially spaced-apart facing relationship, and, in the closed condition of the clamping jaws, the clamping jaws being mutually inwardly resiliently deformed sufficiently to bring the inner clamp-tip surfaces into close proximity and to place the catheter accommodation recesses in aligned opposition;
        a compressible sealing sleeve retained between the clamping jaws in the catheter accommodation recesses, in the open condition of the clamping jaws, the free end of the catheter entered into the catheter passage from the access opening being slidably receivable in the sealing sleeve from the inner opening to the catheter passageway, and, in the closed condition of the clamping jaws, the exterior of the free end of the catheter being gripped mechanically through the sealing sleeve by the catheter accommodation recesses and the sealing sleeve being urged by the clamping jaws into a fluid seal about the exterior of the free end of the catheter;
    a fluid-coupling element configured to selectively effect fluid communication with the free end of the catheter when retentively attached thereto, the fluid-coupling element movably coupled to the catheter-receiving element for movement relative thereto between a catheter-capture condition and a
    catheter-receiving condition, the fluid-coupling element further comprising:
        a fluid-coupling element actuation handle, comprising:
            an outer end configured to selectively effect fluid communication with the free end of the catheter when the free end of the catheter is attached to the connection hub; and
            an abutment end opposite the outer end of the fluid-coupling element actuation handle, the abutment end of the fluid-coupling element actuation handle secured to the abutment end of the catheter-receiving element actuation handle and enabling relative rotation of the fluid-coupling element and the catheter-receiving element between a catheter-receiving condition of the connection hub, wherein the free end of the catheter is admittable into the connection hub and a catheter-capture condition of the connection hub, wherein the connection hub is attached to the free end of the catheter; and
        a clamp-actuation socket, opening at a first end thereof on the abutment end of the fluid-coupling element actuation handle and communicating at the opposite second end thereof with the outer end of the coupling element, the clamp-actuation socket being configured to admit through the first end thereof the clamping jaws in the open condition thereof when the connection hub is in the catheter-receiving condition thereof, and the clamp-actuation socket being rotatable with the fluid-coupling element about the clamping jaws into the catheter-capture condition of the connection hub urging the clamping jaws into the closed condition thereof; and
    a determinant assembly comprising at least one element restricting movement of the fluid-coupling element relative to the catheter-receiving element.

2. The connection hub of claim 1, wherein the at least one element of the determinant assembly comprises a rotational engagement element and a rotational stop element cooperatively engaging the rotational engagement element, wherein the fluid-coupling element is secured rotatably to the catheter-receiving element.

3. The connection hub of claim 2, wherein the rotational engagement element is disposed upon a planar interface surface of the fluid-coupling element adjacently opposed to another planar interface surface of the catheter-receiving element, and the rotational stop element is disposed upon the another planar interface surface of the catheter-receiving element.

4. The connection hub of claim 2, wherein the rotational engagement element is disposed upon a planar interface surface of the catheter-receiving element adjacently opposed to another planar interface surface of the fluid-coupling element, and the rotational stop element is disposed upon the another planar interface surface of the fluid-coupling element.

5. The connection hub of claim 2, wherein the rotational engagement element is an arch-shaped channel comprising two sidewalls and at least one end stop extending between the two sidewalls.

6. The connection hub of claim 5, wherein the at least one end stop is configured to prevent rotational movement of the rotational stop element beyond the catheter-capture condition in a direction defined from the catheter-capture condition to the catheter-receiving condition.

7. The connection hub of claim 2, wherein the rotational engagement element is a channel comprising first and second end stops, the first end stop configured to prevent rotational movement of the rotational stop element beyond the catheter-receiving condition in a direction defined from the catheter-capture condition to the catheter-receiving condition, and the second end stop configured to prevent rotational movement of the rotational stop element beyond the catheter-capture condition in a direction defined from the catheter-receiving condition to the catheter-capture condition.

8. The connection hub of claim 3, wherein the rotational stop element is a stub extending from the another planar surface of the catheter-receiving element and having a cylindrically shaped surface.

9. The connection hub of claim 8, wherein the stub is configured to prevent rotational movement of the rotational engagement element beyond the catheter-receiving condition in a direction defined from the catheter-capture condition to the catheter-receiving condition.

10. The connection hub of claim 8, wherein the stub is configured to prevent rotational movement of the rotational engagement element beyond the catheter-receiving condition in a direction defined from the catheter-capture condition to the catheter-receiving condition and configured to prevent rotational movement of the rotational engagement element beyond the catheter-capture condition in a direction defined from the catheter-receiving condition to the catheter-capture condition.

11. The connection hub of claim 1, wherein the determinant assembly comprises a rotational engagement element and a rotational stop element cooperatively engaging the rotational engagement element.

12. The connection hub of claim 11, wherein the rotational engagement element extends into a planar interface surface of the catheter-receiving element, and the rotational stop element extends from a planar interface surface of the fluid-coupling element.

13. The connection hub of claim 11, wherein the rotational engagement element comprises at least one end stop configured to prevent rotational movement of the rotational stop element beyond the catheter-receiving condition in a direction defined from the catheter-capture condition to the catheter-receiving condition.

14. The connection hub of claim 1, wherein the at least one element of the determinant assembly comprises a rotational engagement element coupled to the catheter-receiving element, and a rotational stop element cooperatively engaging the rotational engagement element and coupled to the fluid-coupling element.

15. The connection hub of claim 14, wherein the rotational engagement element extends into a planar interface surface of the catheter-receiving element and the rotational stop element extends from a planar interface surface of the fluid-coupling element.

16. The connection hub of claim 14, wherein the rotational engagement element comprises at least one end stop configured to prevent rotational movement of the rotational stop element beyond the catheter-receiving condition in a direction defined from a catheter-capture condition to a catheter-receiving condition.

17. The connection hub of claim 14, wherein the rotational engagement element is a channel comprising two end stops, the first end stop configured to prevent rotational movement of the rotational stop element beyond the catheter-receiving condition in a direction defined from a catheter-capture condition to a catheter-receiving condition, and the second end stop configured to prevent rotational movement of the rotational stop element beyond the catheter-capture condition in a direction defined from the catheter-receiving condition to the catheter-capture condition.

18. A method of making the connection hub of claim 1 having a determinant assembly feature for attaching a catheter, the method comprising:
  forming the catheter-receiving element configured to slidably admit a free end of a catheter and having a first portion of the determinant assembly;
  forming the fluid-coupling element configured to selectively effect fluid communication with the free end of the catheter when retentively attached thereto and having a second portion of the determinant assembly; and
  rotatably securing the fluid-coupling element to the catheter-receiving element for movement relative thereto between the catheter-receiving condition and the catheter-capture condition.

19. The method of claim 18, further comprising forming the first portion of the determinant assembly to comprise a rotational engagement element, and forming the second portion of the determinant assembly to comprise a rotational stop element cooperatively engaging the rotational engagement element.

20. A method of connecting a free end of a catheter to the connection hub of claim 1, the method comprising:
  receiving the free end of the catheter slidably into the catheter-receiving element configured to admit the free end of the catheter therein in the catheter-receiving condition, the catheter-receiving element having a first portion of the determinant assembly and rotatably securable to the fluid-coupling element for movement relative thereto between the catheter-receiving condition and the catheter-capture condition, the fluid-coupling element having a second portion of the determinant assembly; and
  securing the fluid-coupling element relative to the catheter-receiving element into the catheter-capture condition to effect fluid communication with the free end of the catheter.

21. A method of utilizing a connection hub for connecting the free end of a catheter thereto, wherein the method comprises utilizing the connection hub of claim 1.

* * * * *